United States Patent [19]
Lim et al.

[11] Patent Number: 5,876,464
[45] Date of Patent: Mar. 2, 1999

[54] HAIR DYEING WITH N-(4-AMINOPHENYL) PROLINEAMIDE, COUPLERS, AND OXIDIZING AGENTS

[75] Inventors: Mu-Ill Lim, Trumbull; Margaret A. Popp, Branford; Yuh-Guo Pan, Stamford, all of Conn.

[73] Assignee: Bristol-Myers Squibb Company, New York, N.Y.

[21] Appl. No.: 24,770

[22] Filed: Feb. 17, 1998

[51] Int. Cl.$^6$ ....................................... A61K 7/13
[52] U.S. Cl. ........................... 8/409; 8/408; 8/423; 8/574
[58] Field of Search .................................. 8/406, 408, 409, 8/410, 411, 412, 423, 574; 548/537

[56] References Cited

U.S. PATENT DOCUMENTS

| | | | |
|---|---|---|---|
| 3,164,597 | 1/1965 | Leonard | 548/537 |
| 3,250,771 | 5/1966 | Leonard et al. | 548/537 |
| 5,019,130 | 5/1991 | Flood | 8/423 |
| 5,278,034 | 1/1994 | Ohki et al. | 548/537 |
| 5,328,812 | 7/1994 | Haijima et al. | 430/388 |
| 5,380,625 | 1/1995 | Mihayashi et al. | 430/388 |

*Primary Examiner*—Caroline D. Liott
*Attorney, Agent, or Firm*—Morton S. Simon

[57] ABSTRACT

N-(4-Aminophenol) prolineamide and cosmetically acceptable salts thereof are useful as primary intermediates in oxidative hair dyeing. Compositions which contain a hair dye produced by oxidatively coupling N-(4-aminophenol) prolineamide with a coupler in the presence of an oxidizing agent are applied to the hair in oxidative hair dyeing processes.

8 Claims, No Drawings

HAIR DYEING WITH N-(4-AMINOPHENYL) PROLINEAMIDE, COUPLERS, AND OXIDIZING AGENTS

BACKGROUND OF THE INVENTION p-Phenylenediamine plays a very important role in oxidative hair coloring. A majority of shades are obtained with dyes based on this primary intermediate. However, as noted in U.S. Pat. Nos. 5,599,353 and 5,538,516, the use of p-phenylenediamine is currently being questioned for toxicological reasons. Thus, the art has need for an alternative to p-phenylenediamine.

GB 2,239,265A teaches that 2-(2-hydroxyethyl)-p-phenylenediamine can be employed as a potential replacement for p-phenylenediamine. U.S. Pat. No. 5,538,516 also describes the use of 2-(hydroxyalkoxy)-p-phenylenediamine as a p-phenylenediamine substitute. There are however, many limitations to the use of these compounds and the need for a satisfactory alternative to p-phenylenediamine remains unsatisfied. The present invention seeks to satisfy that need.

SUMMARY OF THE INVENTION

The present invention provides the novel compound, N-(4-aminophenyl) prolineamide (1).

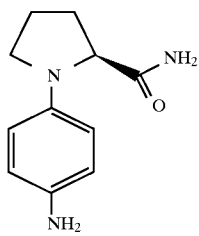

N-(4-Aminophenyl) prolineamide (1) or a cosmetically acceptable salt thereof is useful as a primary intermediate in oxidative hair dyeing. Compositions containing N-(4-aminophenyl)prolineamide or a cosmetically acceptable salt thereof, for oxidative hair coloring, are provided.

As noted earlier, N-(4-aminophenyl) prolineamide (1) is a novel compound. As shown in Table 2 hereof, it couples with conventional couplers to produce ash to neutral brown to blue coloration on gray hair.

One skilled in the art knowing the structures of the primary intermediate N,N-bis(2-hydroxyethyl)-p-phenylenediamine (2) and the novel primary intermediate N-(4-aminophenyl) prolineamide (1) of the present invention would expect that the dyes produced by oxidatively coupling them with the same coupler would have substantially the same color. This is because the structural differences between the two oxidative dyes so produced do not reside in the chromophore moiety and therefor would be expected to have little influence on the dye color.

The present inventors have surprisingly found that dyes produced by coupling N-(4-aminophenyl) prolineamide (1) with conventional couplers undergo a hypsochromic shift as compared to dyes produced by coupling N,N-bis(2-hydroxyethyl)-p-phenylenediamine with the same couplers. N-(4-Aminophenyl) prolineamide (1) should be considered to be a N,N-disubstituted p-phenylenediamine because prolineamide and diethanolamine are both secondary amines. N,N-bis(2-hydroxyethyl)-p-phenylenediamine (2),

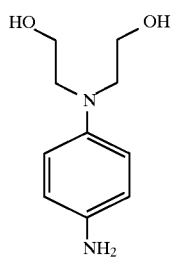

is a N,N-disubstituted p-phenylenediamine that is extensively used in commercial hair coloring products.

For example, N-(4-aminophenyl) prolineamide (1) couples with 2-methyl-1-naphthol to produce a dye which colors gray hair dark violet. In contrast, thereto, N,N-bis(2-hydroxyethyl)-p-phenylenediamine couples with 2-methyl-1-naphthol to surprisingly produce a dye which imparts a blue coloration to gray hair.

N-(4-Aminophenyl) prolineamide (1) couples with 5-amino-2-methylphenol to produce a dye which imparts a red violet coloration to hair while N,N-bis(2-hydroxyethyl)-p-phenylenediamine (2) couples with 5-amino-2-methylphenol to produce a dye which imparts a violet coloration to hair. Examples of colors obtained by coupling N-(4-aminophenyl) prolineamide with other couplers are set forth in Table 2 of the present application.

The novel primary intermediate (1) of the present invention affords numerous advantages, principal of which is the provision of an alternative to p-phenylenediamine in the development of dark red and burgundy shades.

In general, couplers known to be useful in oxidative hair dyeing can be employed in conjunction with the novel primary intermediate of the present invention [N-(4-aminophenol) prolineamide (1)]. Such couplers include, for example, o-aminophenol, resorcinol, 2-chlororesorcinol, 3-aminophenol, 2,4-diaminophenoxyethanol, 1-naphthol, 2-methyl-1-naphthol, 4-chlororesorcinol, 2-methylresorcinol, 5-amino-2-methylphenol, 2-amino-3-hydroxypyridine and mixtures thereof 3-Aminophenol is a particularly preferred coupler. It couples with the novel primary intermediate of the present invention (1) to produce a dye which, as shown in Table 5, possesses excellent wash and light fastness.

2,4-Diaminophenoxyethanol is another preferred coupler. It couples with the novel primary intermediate of the present invention (1) to produce a dye which, as shown in Table 6, imparts a blue color on gray hair and possesses excellent fastness properties.

5-Amino-2-methylphenol is yet another preferred coupler. It couples with the novel primary intermediate of the present invention (1) to produce a dye having a dark violet color. This dye allows one to formulate dark red and burgundy shades without relying on the use of p-phenylenediamine.

The combination of 4-aminophenol and 5-amino-2-methylphenol when coupled with the novel intermediate of the present invention (1) produces a dye that colors hair dark red. The resulting shade is very similar to that of the dark red produced by commercial products containing p-phenylenediamine, 4-aminophenol as oxidation dye precursors and 5-amino-2-methylphenol as a coupler.

The following example is offered to illustrate a procedure for preparing the novel primary intermediate of the present invention (1).

EXAMPLE 1

Synthesis of N-(4-aminophenol) prolineamide (1)

1-Fluoro-4-nitrobenzene (3) (14.1 g, 100 mmole) is stirred with L-proline (4) (11.5 g, 100 mmole) and potassium carbonate (17 g, 120 mmole) in DMF (200 ml) at 60° C. for 18 hours. The reaction is cooled to room temperature. The solvent is evaporated under vacuum and the residue is taken up into ethyl acetate (500 ml). The organic phase is washed with saturated NaCl solution (500 ml). The phases are separated and the aqueous phase is acidified to pH of ~2 with 10% HCl solution (aq). The aqueous phase is extracted with ethyl acetate (2×500 ml). The combined organic phase is dried over $MgSO_4$, filtered, and evaporated under vacuum to leave a yellow solid. The crude material is then recrystallized from ethyl acetate/hexane to produce compound (5) (19.4 g, 82% yield) as a yellow solid: mp. 14°5–147° C.

Compound (5) (19.3 g, 81.8 mmole) is stirred with triethylamine (12.5 ml, 90.0 mmole) and ethyl chloroformate (8.6 ml, 90.0 mmole) in 27.3 ml of TBF (0.3M) at a temperature of −10° C. for 20 minutes. The resulting solution is then saturated with ammonia gas at −10° C. The mixture is allowed to warm up to room temperature overnight (18 hrs). The solvent is evaporated under vacuum and the residue is taken up into ethyl acetate (500 ml) and saturated NaCl solution (250 ml). Ethyl acetate layer is separated. The aqueous phase is extracted with ethyl acetate (500 ml). The organic phases are combined, dried over $MgSO_4$, filtered, and evaporated under vacuum to leave a yellow solid. The crude material is then recrystallized from ethyl acetate/hexane to produce compound (6) (11.9 g, 62% yield) as a yellow solid: mp 180°–181° C.; $^1$H NMR (300 MHz; DMSO-$d_6$) δ 2.01 (m, 3H), 2.28 (m, 1H), 3.38 (m, 1H), 3.66 (m, 1H), 4.20 (d, 1H, 8.7 Hz), 6.57 (d, 2H, J=9.0 Hz), 7.20 (s, 1H), 7.57 (s, 1H), 8.09 (d, 2H, J=9.0 Hz); m/z 235 ($M^+$).

Compound (6) (6.15 g, 26.1 mmole) is then hydrogenated at 60 psi of hydrogen in the presence of 10% Pd on carbon (0.62 g) in ethanol (150 ml, 0.17M solution) for 4 hours at room temperature. The solution is then filtered through a pad of Celite, evaporated, and the crude material is recrystallized from ethyl acetate/hexane to give compound (1) (4.17 g, 78% yield) as a light brown solid: mp 160°–161° C.; $^1$H NMR (300 MHz, DMSO-$d_6$) δ 1.91 (m, 3H), 2.14 (m, 1H), 3.01 (m, 1H), 3.47 (m, 1H), 3.61 (d, 1H, J=8.4 Hz), 4.31 (s, 2H,) 6.25 (d, 2H, J=7.8 Hz), 6.46 (d, 2H, J=7.8 Hz), 6.94 (s, 1H), 7.18 (s, 1H); m/z 205 ($M^+$).

REACTION SCHEME

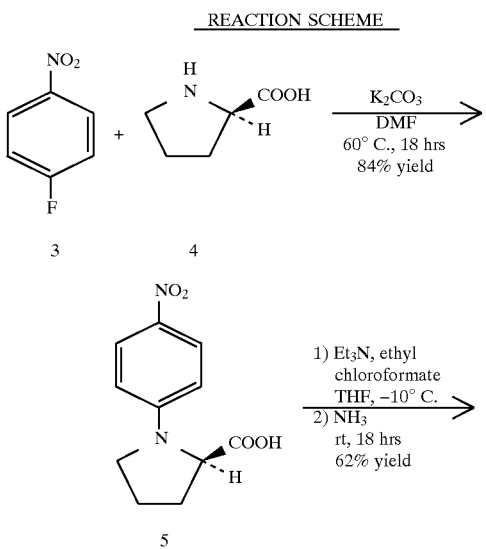

-continued
REACTION SCHEME

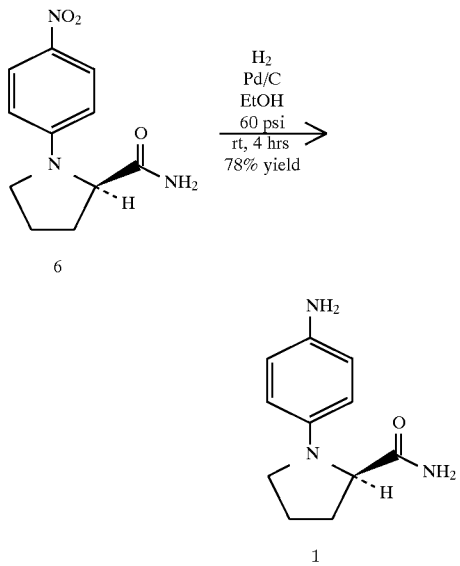

TABLE 1

| Dye Composition | |
|---|---|
| Ingredient | Percentage/Weight |
| Cocamidopropyl betaine | 17.00 |
| Ethanolamine | 2.00 |
| Oleic Acid | 0.75 |
| Citric Acid | 0.10 |
| Ammonium hydroxide | 5.00 |
| Behentrimonium chloride | 0.50 |
| Sodium sulfite | 0.10 |
| EDTA | 0.10 |
| Erythorbic acid | 0.40 |
| Primary Intermediate (1 or 2) | 5 mmole |
| Coupler | 5 mmole |
| Water | QS 100.00 |

Dyeing Procedure

Dye compositions in accordance with Table 1 were prepared. Each dye composition contained 5 mmole of primary intermediate (1 or 2) and 5 mmole of coupler. The dye composition was mixed with 100 g of 20 volume hydrogen peroxide. The resulting mixture was applied to gray hair and permitted to remain in contact with the hair for 30 minutes. The thus dyed hair was then shampooed and rinsed with water and dried.

Table 2, which follows, shows the Hunter L, a, b values and the colors obtained for each of the coupler primary intermediate combinations evaluated.

TABLE 2

Colors and Hunter values resulting from coupling the primary intermediate of the present invention (1) with various couplers.

| EX. # | P | Coupler | L | a | b | Color Description |
|---|---|---|---|---|---|---|
| 1 | 1 | o-Aminophenol | 24.79 | 1.45 | 3.44 | Ash |
| 2 | | Resorcinol | 21.58 | 2.57 | 2.78 | Neutral brown |
| 3 | | 2-Chlororesorcinol | 22.75 | 2.78 | 2.96 | Neutral brown |
| 4 | | m-Aminophenol | 18.03 | 0.90 | −1.01 | Dark ash brown |

TABLE 2-continued

Colors and Hunter values resulting from coupling the primary intermediate of the present invention (1) with various couplers.

| EX. # | P | Coupler | L | a | h | Color Description |
|---|---|---|---|---|---|---|
| 5 | | 2,4-Diamino-phenoxyethanol | 15.98 | 0.91 | −3.13 | Blue |
| 6 | | 2-Methyl-1-naphthol | 21.21 | 2.38 | −6.05 | Dark violet |
| 7 | | 2-Methylresorcinol | 20.71 | 3.27 | 2.12 | Reddish brown |
| 8 | | 5-Amino-2-methyl-phenol | 20.80 | 5.29 | −3.69 | Red violet |
| 9 | | 2-Amino-3-hydroxypyridine | 17.48 | 3.07 | 0.42 | Violet red |
| 10 | 2 | 2-Methyl-1-naphthol | 18.52 | 0.85 | −6.63 | Blue |
| 11 | | 2-Methylresorcinol | 18.83 | 1.65 | 0.24 | Dark brown |
| 12 | | 5-Amino-2-methyl-phenol | 17.45 | 1.86 | −4.19 | Violet |
| 13 | | 2-Amino-3-hydroxypyridine | 17.45 | 1.52 | −0.72 | Dark violet brown |

EXAMPLE 14

Composition of Red Shade

A dye composition (A) was prepared. The formulation of A is set forth in Table 3 which follows. A second dye composition (B) comprises a commercial product (Clairol's Hydrience, Shade 32, Dark Red) containing 4-aminophenol, p-phenylenediamnine and 5-amino-2-methylphenol as the oxidation dye precursors. Compositions A and B were then utilized to color gray hair. The two compositions imparted the same shade to gray hair. Tristimulus values were determined for hair dyed with Composition A and hair dyed with Composition B. The tristimulus values are reported in Table 4 which follows.

Referring now to Table 4, it should be noted that L indicates lightness and a and b are the chromaticity coordinates. The a and b values indicate color direction: +a is the red direction, −a is the green direction, +b is the yellow direction and −b is the blue direction. Note that in Table 4, hair dyed with Composition A and hair dyed with Composition B show almost identical L and a values. Although b values are different, the difference is not significant.

TABLE 3

Dye Compositions A and B

| | A Composition (%) | B Composition (%) |
|---|---|---|
| Cocamidopropyl betaine | 17.00 | Commercial product containing 4-aminophenol, p-phenylenediamine, and 5-amino-2-methylphenol as the oxidation dye precursors. |
| Ethanolamine | 2.00 | |
| Oleic Acid | 0.75 | |
| Citric Acid | 0.10 | |
| Ammonium hydroxide | 5.00 | |
| Behentrimonium chloride | 0.50 | |
| Sodium sulfite | 0.10 | |
| EDTA | 0.10 | |
| Erythorbic acid | 0.40 | Dyeing time was 20 min. |
| Compound 1 | 1.03 | |
| 4-Aminophenol | 0.55 | |
| 5-Amino-2-methylphenol | 1.23 | |
| Water | QS 100.00 | |
| Color | Dark red | Dark red |

TABLE 4

Tristimulus Values for Hair Dyed with Formulation A and Hair Dyed with Formulation B.

| Composition | Hair type | L | a | b |
|---|---|---|---|---|
| A | gray | 18.76 | 6.02 | 2.41 |
| B | gray | 18.84 | 6.06 | 1.55 |

EXAMPLE 15

Wash and Light Fastness

To test the degree of resistance to shampooing, hair colored with Composition A and hair colored with Composition B were immersed and shaken for three hours in a 10% solution of Herbal Essences® Shampoo. Light fastness was tested by subjecting the washed, dyed hair to a fadeometer (Atlas Ci 35 Xenon) for 72 hours. The exposure level is 77.8 KJ/m$^2$. Tristimulus values and overall color changes were then determined. The results are set forth in Tables 5 and 6 which follow.

It is evident from the data of Tables 5 and 6 that in the case of the composition containing the novel primary intermediate of the present invention (1), the ΔE values range from 1.46 to 2.72. In contrast thereto, in the case of compositions containing N,N-bis(2-hydroxyethyl)-p-phenylenediamine (2) as the primary intermediate, the ΔE values varied from 1.73 to 4.12. ΔE indicates the size of the color difference. The smaller the ΔE value, the better the wash and light fastness.

ΔE is defined as $\sqrt{\Delta L^2 + \Delta a^2 + \Delta b^2}$.

TABLE 5

Tristimulus Values of Shampoo and Light Fastness Studies with 3-aminophenol

| | | Before | | | After | | | |
|---|---|---|---|---|---|---|---|---|
| 3-Aminophenol | PI | L | a | b | L | a | b | ΔE |
| Wash 5 hr | 1 | 18.03 | 0.90 | −1.01 | 20.19 | 0.73 | 0.27 | 2.52 |
| | 2 | 16.65 | 0.01 | −1.89 | 18.33 | −0.17 | −1.53 | 1.73 |
| Light 72 hr | 1 | 18.03 | 0.90 | −1.01 | 18.17 | 1.12 | 0.43 | 1.46 |
| | 2 | 16.65 | 0.01 | −1.89 | 18.54 | −0.02 | −0.39 | 2.41 |

PI: Primary Intermediate, $\Delta E = \sqrt{\Delta E = \Delta L^2 + \Delta a^2 + \Delta b^2}$

TABLE 6

Tristimulus Values of Shampoo and Light Fastness Studies with Blue Coupler*

| | | Before | | | After | | | |
|---|---|---|---|---|---|---|---|---|
| Blue Coupler | PI | L | a | b | L | a | b | ΔE |
| Wash 5 hr | 1 | 15.98 | 0.91 | −3.13 | 17.81 | −0.11 | −4.87 | 2.72 |
| | 2 | 15.11 | 0.71 | −3.11 | 18.7 | −0.23 | −4.89 | 4.12 |
| Light 72 hr | 1 | 15.98 | 0.91 | −3.13 | 16.49 | −0.13 | −1.61 | 1.91 |
| | 2 | 15.11 | 0.71 | −3.11 | 16.51 | −0.43 | −2.03 | 2.10 |

*2,4-diaminophenoxyethanol.

It should be appreciated that the novel oxidative dyes of the present invention produced by reacting the novel N-(4-aminophenyl) prolineamide primary intermediate with a coupler in the presence of an oxidizing agent can be employed in conjunction with one or more other primary intermediates used in oxidative hair dyeing, with the same or different couplers being employed. Preferred primary intermediates are 4-aminophenol and 4-amino-3-methylphenol. 4-Aminophenol, when used in conjunction with the novel dye produced by oxidative coupling of 2-methyl-5-aminophenol with N-(4-aminophenyl) prolineamide, advantageously produces a dark red shade, as noted earlier.

What is claimed is:

1. A process for the oxidative dyeing of hair comprising applying to the hair N-(4-aminophenyl) prolineamide as a primary intermediate in an oxidative hair dye process.

2. In an oxidative hair dye system comprising a primary intermediate, a coupler and an oxidizing agent which is suitable for the oxidative dyeing of hair, the primary intermediate reacting with the coupler in the presence of the oxidizing agent to produce an oxidative hair dye, wherein the improvement comprises the primary intermediate is N-(4-aminophenyl) prolineamide or a cosmetically acceptable salt thereof.

3. A hair dye produced by reacting N-(4-aminophenyl) prolineamide, or a cosmetically acceptable salt thereof, with a coupler, in the presence of an oxidizing agent which is suitable for the oxidative dyeing of hair.

4. The hair dye, according to claim 3, wherein the coupler is selected from the group consisting of o-aminophenol, resorcinol, 2-chlororesorcinol, 4-chlororesorcinol, 3-aminophenol, 2,4-diaminophenoxyethanol, 1-naphthol, 2-methyl-1-naphthol, 2-methyl resorcinol, 2-methyl-5-aminophenol, 2-amino-3-hydroxypyridine and mixtures thereof.

5. The hair dye according to claim 3, wherein the coupler is 3-aminophenol.

6. The hair dye according to claim 3, wherein the coupler is 2,4-diaminophenoxyethanol.

7. The hair dye according to claim 3, wherein the coupler is 2-methyl-5-aminophenol.

8. An aqueous hair dye composition comprising a tinctorially effective amount of a first hair dye produced by oxidatively coupling N-(4-aminophenyl) prolineamide with a first coupler in the presence of an oxidizing agent which is suitable for the oxidative dyeing of hair, and a tinctorially effective amount of a second hair dye produced by oxidatively coupling 4-aminophenol and/or 4-amino-3-methyl phenol with a second coupler in the presence of an oxidizing agent which is suitable for the oxidative dyeing of hair, the first and second couplers being the same or different.

* * * * *